US00PP26053P3

(12) United States Plant Patent
Meilland

(10) Patent No.: US PP26,053 P3
(45) Date of Patent: Nov. 10, 2015

(54) FLORIBUNDA ROSE PLANT NAMED 'MEICKINAVA'

(50) Latin Name: *Rosa hybrida*
Varietal Denomination: Meickinava

(71) Applicant: CP DELAWARE, INC., Wilmington, DE (US)

(72) Inventor: Alain A. Meilland, Antibes (FR)

(73) Assignee: CP DELAWARE, INC., Wilmington, DE (US)

( * ) Notice: Subject to any disclaimer, the term of this patent is extended or adjusted under 35 U.S.C. 154(b) by 179 days.

(21) Appl. No.: 13/998,702

(22) Filed: Nov. 26, 2013

(65) Prior Publication Data

US 2015/0150166 P1 May 28, 2015

(51) Int. Cl.
*A01H 5/02* (2006.01)

(52) U.S. Cl.
USPC ..... Plt./151

(58) Field of Classification Search
USPC ..... Plt./101, 141, 151
See application file for complete search history.

*Primary Examiner* — Susan McCormick Ewoldt
(74) *Attorney, Agent, or Firm* — Buchanan, Ingersoll & Rooney PC

(57) ABSTRACT

A new and distinct Floribunda rose plant is provided that forms on a substantially continuous basis blossoms having an intense deep red coloration. The growth habit is bushy with the formation of strong vegetation. The vegetation is very dense and bears a glossy aspect on the upper surface. The plant has been found to grow well on its own roots. No particular disease problem has been observed. The plant is particularly well suited for providing attractive ornamentation in parks and gardens.

1 Drawing Sheet

Figures 1, 2, 3, 4, 5, 6, 7, 8, 9, 10, 11, 12, 13, 14, 15, 16, 17:
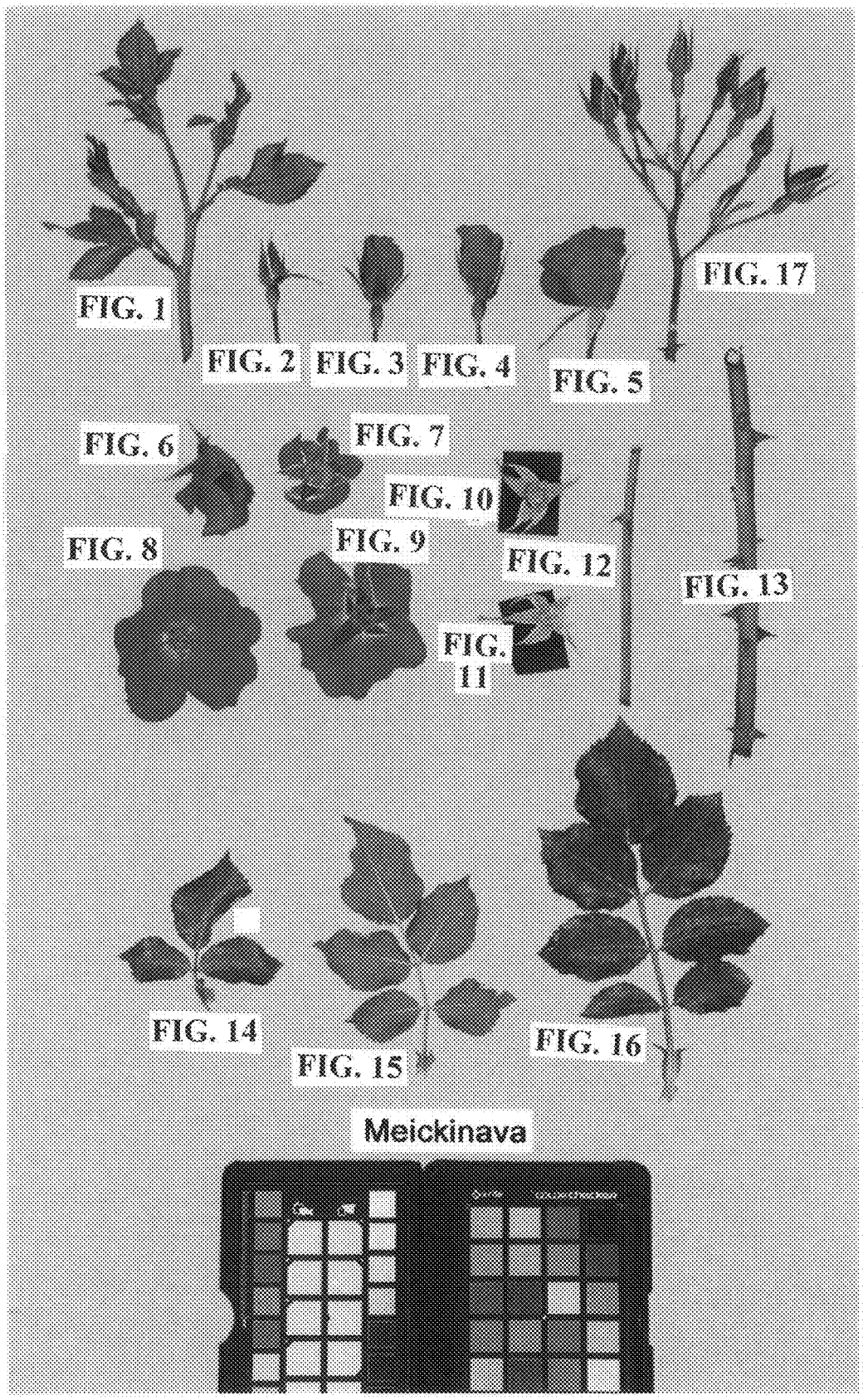

Botanical/commercial classification: *Rosa hybrida*/Floribunda Rose Plant.

Varietal denomination: cv. Meickinava.

SUMMARY OF THE INVENTION

The new variety of *Rosa hybrida* Hybrid Tea rose plant was created by artificial pollination wherein two parents were crossed which previously had been studied in the hope that they would contribute the desired characteristics. The female parent (i.e., the seed parent) was the 'Noacas' variety (non-patented in the United States). The male parent (i.e., the pollen parent) was an unnamed and unreleased seedling (non-patented in the United States).

The parentage of the new variety can be summarized as follows:

'Noacas'×Unnamed Seedling.

The seeds resulting from the above pollination were sown and small plants were obtained which were physically and biologically different from each other. Selective study resulted in the identification of a single plant of the new variety.

It was found that the new Floribunda rose plant of the present invention:

(a) displays a bushy growth habit with strong vegetation,
(b) forms in abundance on a substantially continuous basis attractive single blossoms having an intense deep red coloration,
(c) grows well on its own roots,
(d) exhibits attractive dense glossy dark green foliage, and
(e) is particularly well suited for providing attractive distinctive ornamentation in parks and gardens.

The blooming tends to commence medium in the season, during observations to date. The blossoms display a distinctive forceful deep red coloration that contrasts nicely with the coloration of the foliage.

The new variety well meets the needs of the horticultural industry and can be grown to advantage where attractive ornamentation is to be provided.

The new variety can be readily distinguished from other Foribunda rose varieties. For instance, the 'Noacas' parental variety forms dissimilarly colored orange to orange-red blossoms combined with a more spreading growth habit. The male parent displays a ground cover growth habit and forms double flowers.

The new variety additionally can be readily distinguished from the 'Meizerbil' variety (U.S. Plant Pat. No. 20,168) and the 'Meizmea' variety (U.S. Plant Pat. No. 20,175). More specifically, the 'Meizerbil' novelty forms semi-double blossoms and the 'Meizmea' variety forms blossoms having a pronounced spot at the base of the petals.

The new variety has been found to undergo asexual propagation in France by a number of routes, including budding, grafting, and the use of cuttings. Asexual propagation by the above-mentioned techniques at Le Cannet des Maures, Var, France, has shown that the characteristics of the new variety are stable and are strictly transmissible by such asexual propagation from one generation to another. Accordingly, the new variety undergoes asexual propagation in a true-to-type manner. The plant grows well on its own roots.

The new variety has been named 'Meickinava'.

BRIEF DESCRIPTION OF PHOTOGRAPH

The accompanying photograph shows as nearly true as it is reasonably possible to make the same, in a color illustration of this character, typical specimens of the plant parts of the new variety. The rose plants of the new variety were approximately two years of age and were observed during June while growing outdoors on their own roots at Le Cannet des Maures, Var, France. Comparative standard color information is included at the base of the photograph.

FIG. 1—illustrates a specimen of a young shoot;

FIG. 2—illustrates a specimen of a floral bud at the opening of the sepals;

FIG. 3—illustrates a specimen of a floral bud wherein the sepals are more fully open;

FIG. 4—illustrates a specimen of a floral bud at the initial opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface;

FIG. 16—illustrates a specimen of a leaf with seven leaflets—plan view—upper surface; and FIG. 17—illustrates a cluster of buds.

DETAILED BOTANICAL DESCRIPTION

The chart used in the identification of the colors is that of The Royal Horticultural Society (R.H.S. Colour Chart—1995 or equivalent). The description is based on the observation of one-year-old plants during May while growing outdoors on their own roots at Le Cannet des Maures, Var, France.

Class: Floribunda.

Plant:

*Growth habit*.—Bushy.

*Height*.—Commonly approximately 35 to 50 cm on average.

*Width*.—Commonly approximately 35 to 50 cm on average.

Branches:

*Color*.—Young stems: near Green Group 146D. Adult wood: near Yellow-Green Group 146C.

*Thorns*.—On young stems: Configuration: with an oval base. Quantity: approximately 5 on average on a stem length of 10 cm. Length: approximately 3 to 6 mm on average. Color: near Greyed-Purple Group 181A, 181B, and 181C. On adult stems: Configuration: slightly curved downwards on the upper surface and concave on the under surface with an oval base. Quantity: approximately 5 on average over a stem length of 10 cm. Length: approximately 6 to 8 mm on average.

Leaves:

*Length*.—Commonly approximately 15 cm on average for a seven-leaflet leaf.

*Width*.—Commonly approximately 10 cm on average for a seven-leaflet leaf.

*Stipules*.—Adnate, pectinate, rather broad, approximately 1.5 cm in length on average, approximately 0.8 cm in width on average, near Green Group 138C on the upper surface, and near Green Group 138C on the under surface.

*Petioles*.—Upper surface: near Green Group 138B in coloration. Under surface: near Green Group 139C in coloration. Texture: non-glandular on the upper surface, and commonly with a few prickles on the under surface.

*Rachis*.—Upper surface: near Green Group 138D in coloration.

*General appearance*.—Very dense with a glossy aspect on the upper surface of the leaflets. Under surface: near Green Group 138C in coloration.

*Leaflets*.—Number: 3, 5 and 7 (most often). Shape: generally oval with an acuminate tip and a rounded base. Size: the terminal leaflets commonly are approximately 4.9 cm in length on average and approximately 3.8 cm in width on average. Serration: slightly denticulate. Texture: physically firm and leathery. Color (young foliage): Upper surface: near Green Group 137A. Under surface: near Green Group 137C. Color (adult foliage): Upper surface: near Green Group 137A. Under surface: near Green Group 137C. Venation pattern: regular with alternate branching from a central main vein.

Inflorescence:

*Number of flowers*.—Commonly approximately 5 to 17 blossoms per stem.

*Peduncle*.—Glandular, approximately 2.7 cm in length on average, approximately 0.2 cm in diameter on average, and near Green Group 138C in coloration.

*Sepals*.—Upper surface: tomentose and near Yellow-Green Group 148C in coloration. Under surface: smooth and near Green Group 143C in coloration. Shape: not longish and rounded at the base. Size: approximately 2 to 2.3 cm in length on average, and commonly approximately 0.5 cm in width at the widest point on average.

*Buds*.—Shape: substantially conical. Size: small. Length: approximately 1 cm on average. Width: approximately 0.9 cm on average at the widest point. Color as calyx breaks: Upper surface: near Red Group 46B suffused with near Red Group 46A, with a spot of near Yellow Group 2D to Yellow-While Group 158D at the base. Under surface: near Red Group 53B suffused with Red Group 53A, with a spot of Yellow Group 2D to Yellow-While Group 158D at the base.

*Flower*.—Shape: cup-shaped. Diameter: commonly approximately 5 to 6 cm on average. Color (in the course of opening): Upper surface: near Red Group 46B suffused with Red Group 46A, with a spot of near Yellow Group 2D to Yellow-White Group 158D at the base. Under surface: near Red Group 53B suffused with near Red Group 53B, with a spot of near Yellow Group 2D to Yellow-While Group 158D at the base. Color (open flower): Upper side: near Red Group 46B suffused with Red Group 46A, with a spot of Yellow Group 2D to Yellow-White Group 158D at the base.

Under side: near Red Group 53B suffused with near Red Group 53A, with a spot of near Yellow Group 2D to Yellow-White Group 158D at the base. Fragrance: none detected. Petal number: approximately 5 on average under normal growing conditions. Petal texture: leathery and somewhat firm. Petal length: approximately 2.3 cm on average. Petal width: approximately 2.2 cm on average. Petal arrangement: imbricated, and without petaloids. Petal drop: good with the petals commonly detaching cleanly before drying. Stamen number: approximately 121 on average. Anthers: regularly arranged around the styles, approximately 1 mm in size on average, and near Greyed-Orange Group 163A in coloration. Filaments: approximately 3 mm in length on average, and near Yellow-White Group 158B in coloration. Pollen: none available for observation. Pistils: approximately 27 on average. Stigmas: approximately 1 mm in size on average, and near Yellow-White Group 158A in coloration. Styles: approximately 4 mm in length on average, and near Green-White Group 157D in coloration. Receptacle: smooth, pitcher-shaped in longitudinal section, approximately 6 mm in length on average, approximately 4 mm in width on average at the widest point, and near Green Group 143C in coloration.

Development:

*Vegetation*.—Strong.

*Blooming*.—Medium season, very abundant and substantially continuous.

*Tolerance to diseases*.—Very good, with no particular susceptibility to common diseases having been encountered during observations to date.

The new 'Meickinava' variety has not been observed under all possible environmental conditions to date. Accordingly, it is possible that the phenotypic expression may vary somewhat with changes in light intensity and duration, cultural practices, and other environmental conditions.

I claim:

1. A new and distinct Floribunda rose plant characterized by the following characteristics:

(a) displays a bushy growth habit with strong vegetation, (b) forms in abundance on a substantially continuous basis attractive single blossoms having an intense deep red coloration, (c) grows well on its own roots, (d) exhibits attractive very dense glossy dark green foliage, and (e) is particularly well suited for providing attractive distinctive ornamentation in parks and gardens;

substantially as shown and described.

* * * * *

Meickinava